(12) United States Patent
Shapiro (10) Patent No.: US 6,981,503 B1
(45) Date of Patent: Jan. 3, 2006

(54) HANDS FREE-ANESTHESIA MASK (76) Inventor: Leon Shapiro, 11 Fairview Rd., Tenafly, NJ (US) 07670

( * ) Notice: Subject to any disclaimer, the term of this patent is extended or adjusted under 35 U.S.C. 154(b) by 0 days.

(21) Appl. No.: 10/990,076

(22) Filed: Nov. 16, 2004

(51) Int. Cl.
A61F 13/00 (2006.01)
(52) U.S. Cl. ................ 128/845; 128/846; 128/207.11; 128/207.17
(58) Field of Classification Search .......... 128/206.27, 128/845, 846, 207.17, 207.11; 601/41, 43, 601/44
See application file for complete search history.

(56) References Cited

U.S. PATENT DOCUMENTS

| RE26,511 E | * | 12/1968 | Hewson | 128/202.16 |
| 3,461,858 A | * | 8/1969 | Michelson | 601/41 |
| 4,226,234 A | * | 10/1980 | Gunderson | 128/205.24 |
| 4,297,999 A | * | 11/1981 | Kitrell | 128/205.16 |
| 5,176,618 A | * | 1/1993 | Freedman | 600/12 |
| 5,494,048 A | * | 2/1996 | Carden | 5/622 |
| 5,632,283 A | * | 5/1997 | Carden | 128/845 |
| 5,893,365 A | * | 4/1999 | Anderson | 128/848 |
| 6,119,694 A | * | 9/2000 | Correa et al. | 128/207.13 |
| 6,200,285 B1 | * | 3/2001 | Towliat | 602/18 |
| 6,805,117 B1 | * | 10/2004 | Ho et al. | 128/201.22 |
| 2003/0062040 A1 | * | 4/2003 | Lurie et al. | 128/203.11 |
| 2005/0000521 A1 | * | 1/2005 | Frank | 128/846 |

* cited by examiner

Primary Examiner—Henry Bennett
Assistant Examiner—Dinnatia Doster-Greene
(74) Attorney, Agent, or Firm—Gary J. Gershik; Cooper & Dunham LLP (57) ABSTRACT A hands-fee anesthesia mask includes a mask for providing anesthesia to the patient, a mask strap for holding the mask against a patient's mouth, and a jaw raising strap for raising the patient's jaw up and forward so as to unobstruct the patient's airway.

7 Claims, 8 Drawing Sheets

HANDS FREE-ANESTHESIA MASK

BACKGROUND OF THE INVENTION

This invention relates generally to the field of anesthesia masks. More, particularly, this invention relates to an anesthesia mask that allows mask ventilation during anesthesia and sedation without using the anesthetist's hands.

During the surgery a patient is usually placed under anesthesia. The most common delivery system consists of the canisters containing the anesthesia gases and oxygen, a system of regulating the gas flow and the patient's breathing, and a device ensuring the potency of the patient's airway for breathing, oxygenation and the delivery of the anesthetic gas mixture. A mask as shown in FIGS. 1 and 2 is one of the devices used for the airway instrumentation during the surgery and anesthesia.

Figure 1:
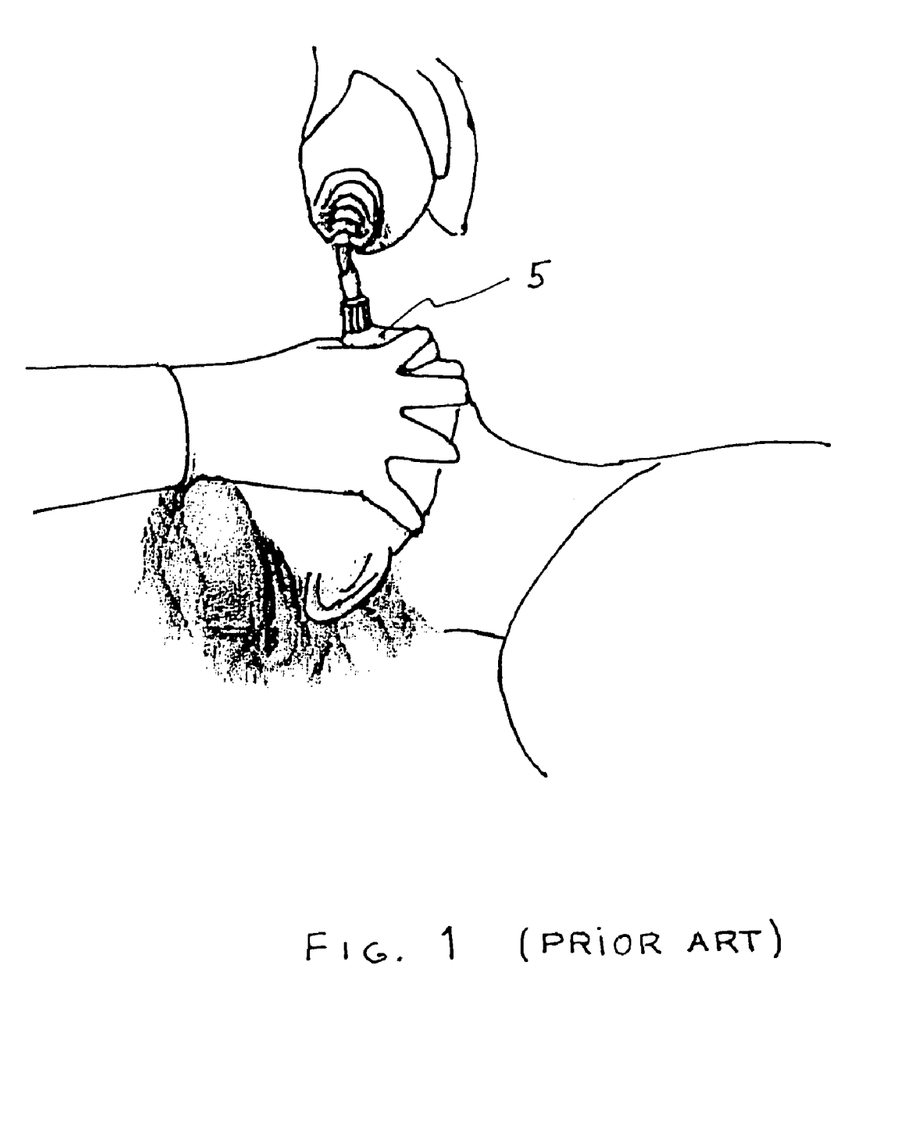
FIG. 1 is a sketch showing an anesthesia mask being held by an anesthetist hand.
Figure 2:
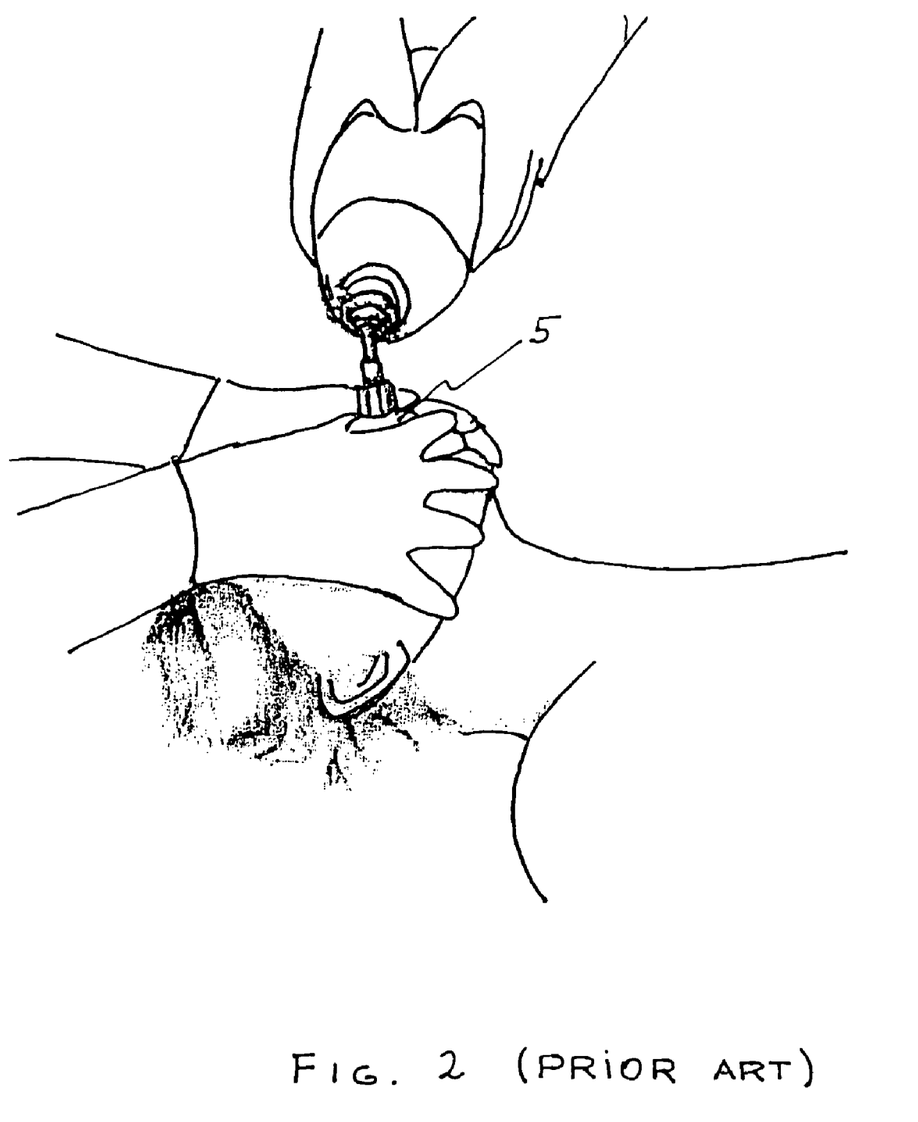
FIG. 2 is a sketch showing an anesthesia mask being held by both hands of an anesthetist.

The use of the mask ventilation requires the constant contact of the anesthetist's hands with the patient, as shown in FIGS. 1 and 2, to hold the mask 5 in place in order to ensure the potency of the airway. Otherwise a very dangerous complication known as the airway obstruction may occur. Today in the majority of cases the use of the commercially available mask straps and/or the head harness still requires the anesthetist to hold and maneuver the mask continually during the surgery.

Figure 3:
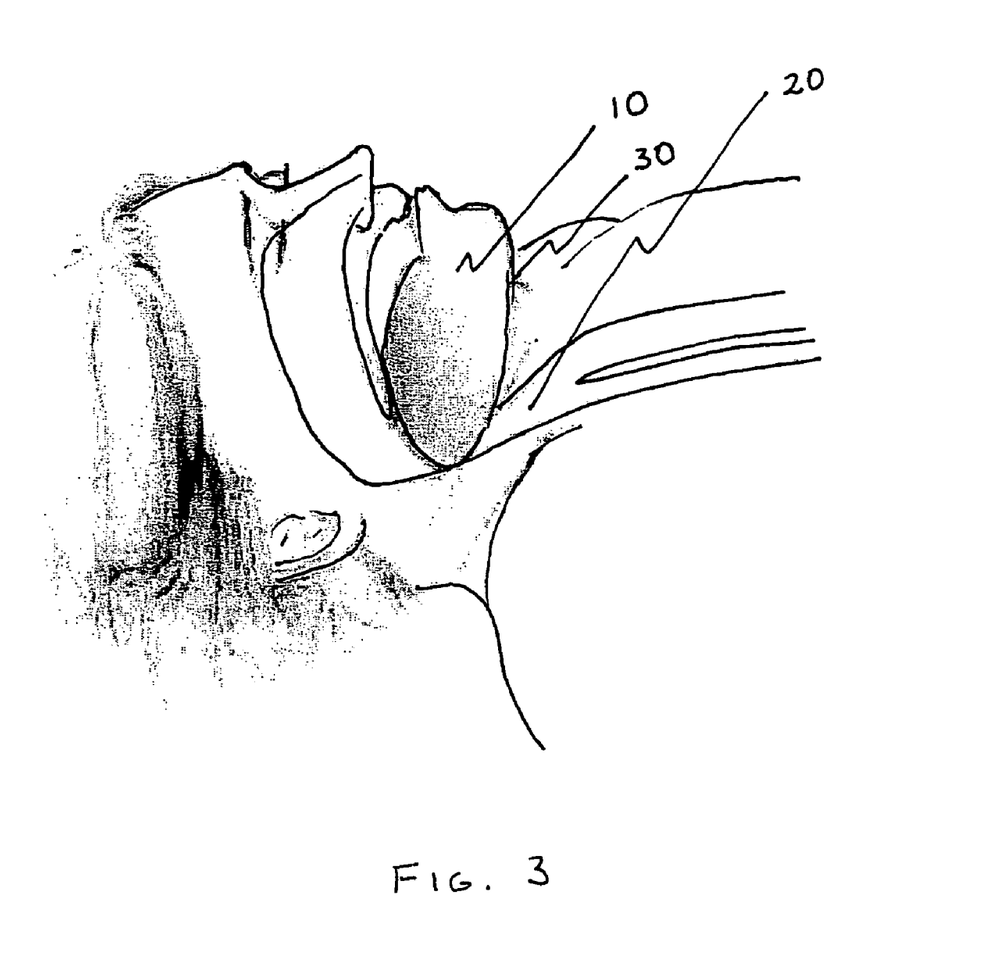
FIG. 3 is a sketch showing an obstructed airway.
Figure 4:
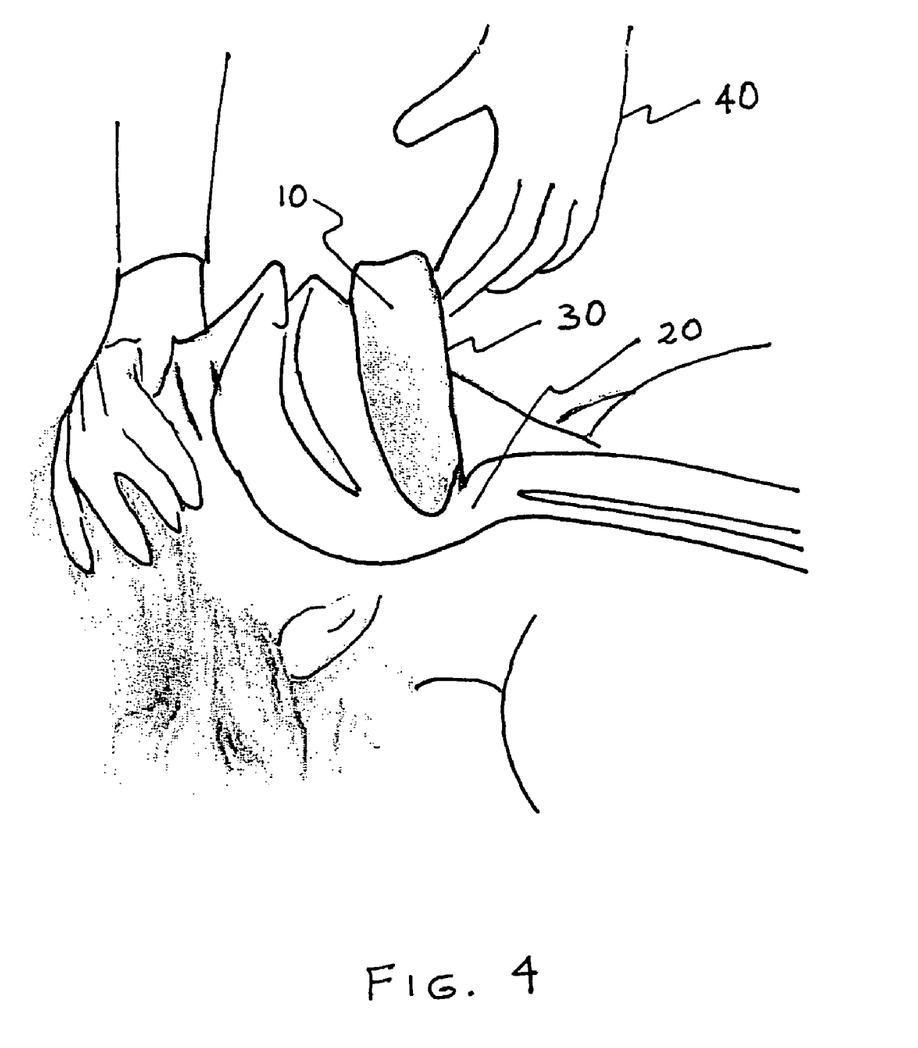
FIG. 4 is a sketch showing an unobstructed airway.

The reason the anesthetist needs to perform continuous mask holding and maneuvering is the human anatomy and physiology. When muscles of the jaw, tongue and upper airway relax due to sedatives and/or muscle relaxants given to the patient for sedation and/or anesthesia, the upper airway (mouth, pharynx, larynx) may become partially obstructed and possibly completely closed, as shown in FIG. 3 wherein when the jaw 30 of the patient drops and the tongue 10 obstructs the airway 20 resulting in snoring (partial obstruction) or apnea (complete inability for oxygen to pass via the upper airway into the lungs). To avoid partial and/or complete obstruction the anesthetist has to perform a maneuver called the "jaw thrust" maneuver. The "jaw thrust" maneuver, illustrated in FIG. 4, is done with one hand 10 moving the jaw 30 up and forward to move the tongue 10 so that the airway 20 is opened. The "jaw thrust" is performed while holding a mask over the patient's mouth and nose to deliver oxygen.

The necessity to hold the mask 5 over the patient's face almost constantly and the inability to perform other tasks during the surgery and anesthesia have led to a significant loss of popularity of the mask anesthetics and the increased use of other airway devices, in some cases more invasive and with more potential side effects and complications.

The present invention is intended to address the problem of the continuous mask holding and to free the hands of the anesthetist for other tasks required during the operation.

SUMMARY OF THE INVENTION

It is an object of the present invention to provide an anesthesia mask that allows mask ventilation during anesthesia and sedation without using the anesthetist's hands.

It is another object of the present invention to provide an improved mask strap for an anesthesia mask that allows hands-free patient ventilation.

It is an advantage of the present invention that less or no anesthesia mask handling is required by the anesthetist.

These and other objects, advantages and features of the invention will become apparent to those skilled in the art upon consideration of the following description of the invention.

According to one aspect of the present invention an apparatus for providing anesthesia to a patient is provided including an anesthesia mask including four protrusions, a mask strap having a head plate and four narrow extensions each including a plurality of holes adapted to attach to the four protrusions of the anesthesia mask, wherein at least two of the four narrow extensions have respective portions of snap fasteners, and a rectangular connecting strap having end portions of snap fasteners attached to the at least two of the four narrow extensions via the respective portions of snap fasteners, wherein the mask strap is adapted to hold the anesthesia mask strap against the patient's mouth and the rectangular connecting strap is adapted to raise the patient's jaw up and forward, thereby unobstructing the patient's airway.

According to another aspect of the present invention two rectangular connecting straps are used to raise the patient's jaw up and forward, thereby unobstructing the patient's airway, and all of the four narrow extensions have respective portions of snap fasteners.

According to a further aspect of the present invention an apparatus for providing anesthesia to a patient is provided including mask means for providing the anesthesia to the patient, mask strap means for holding the mask means against a patient's mouth, and jaw raising means for raising the patient's jaw up and forward so as to unobstruct the patient's airway, wherein the jaw raising means is attached to the mask strap means.

The features of the invention believed to be novel are set forth with particularity in the appended claims. The invention itself however, both as to organization and method of operation, together with further objects and advantages thereof, may be best understood by reference to the following description taken in conjunction with the accompanying drawing.

BRIEF DESCRIPTION OF THE CLAIMS

DETAILED DESCRIPTION OF THE INVENTION

While this invention is susceptible of embodiment in many different forms, there is shown in the drawings and will herein be described in detail specific embodiments, with the understanding that the present disclosure is to be considered as an example of the principles of the invention and not intended to limit the invention to the specific embodiments shown and described. In the description below, like reference numerals are used to describe the same, similar or corresponding parts in the several view of the drawing.

Figure 5:
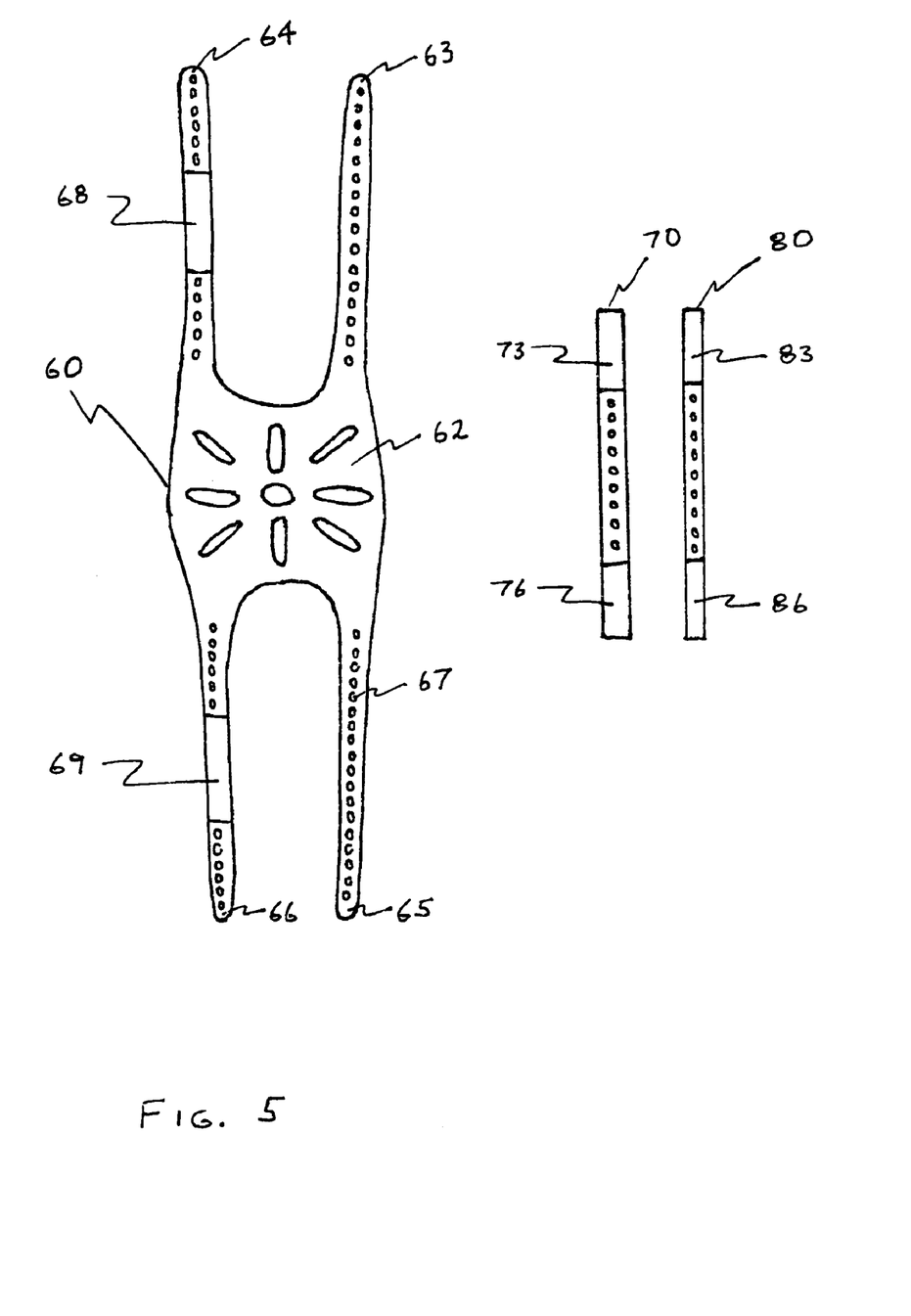
FIG. 5 is a sketch showing a mask strap including two connecting straps according to an embodiment of the present invention.

Turning now to FIG. 5 we see a mask strap 60 and two connecting straps 70 and 80 according to an embodiment of the present invention. The mask strap 60 consists of a head plate 62 with four narrow extensions 63, 64, 65, and 66 projecting out of the head plate 62. The left pair of narrow extensions 64 and 66 are formed to be parallel to the right pair of narrow extensions 63 and 65.

Figure 6:
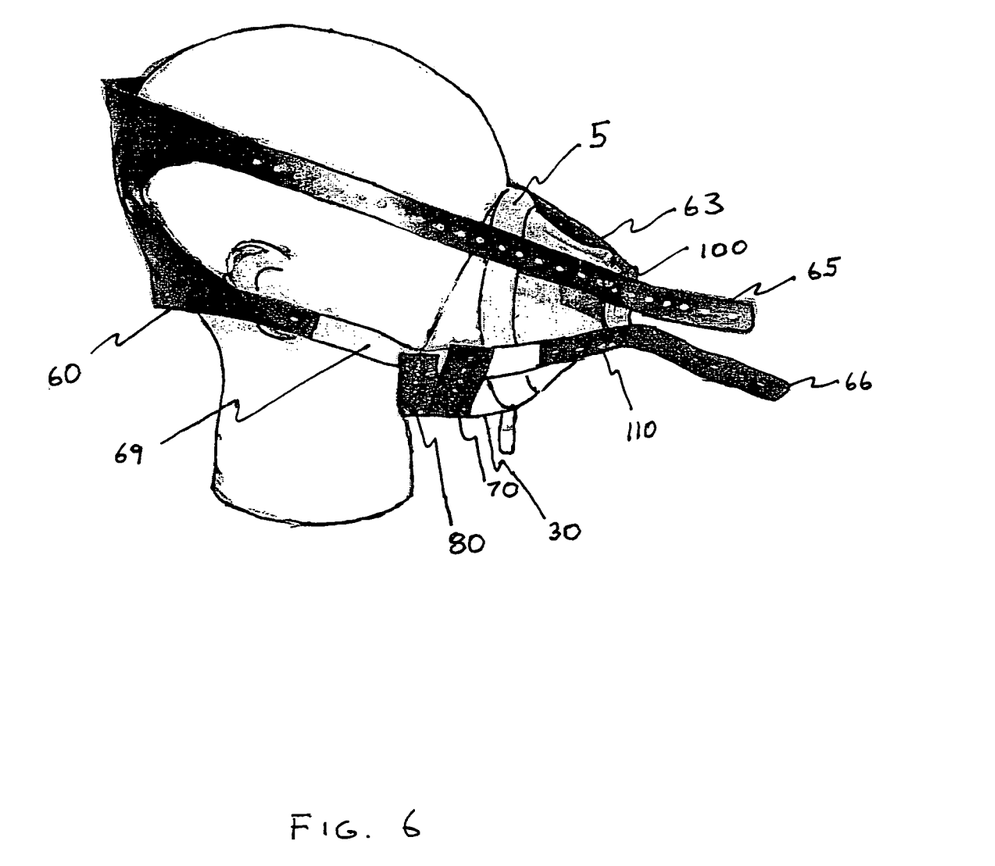
FIG. 6 is a side view of the mask strap, the connecting straps, and the anesthesia mask strapped to a model head according to an embodiment of the present invention.
Figure 7:
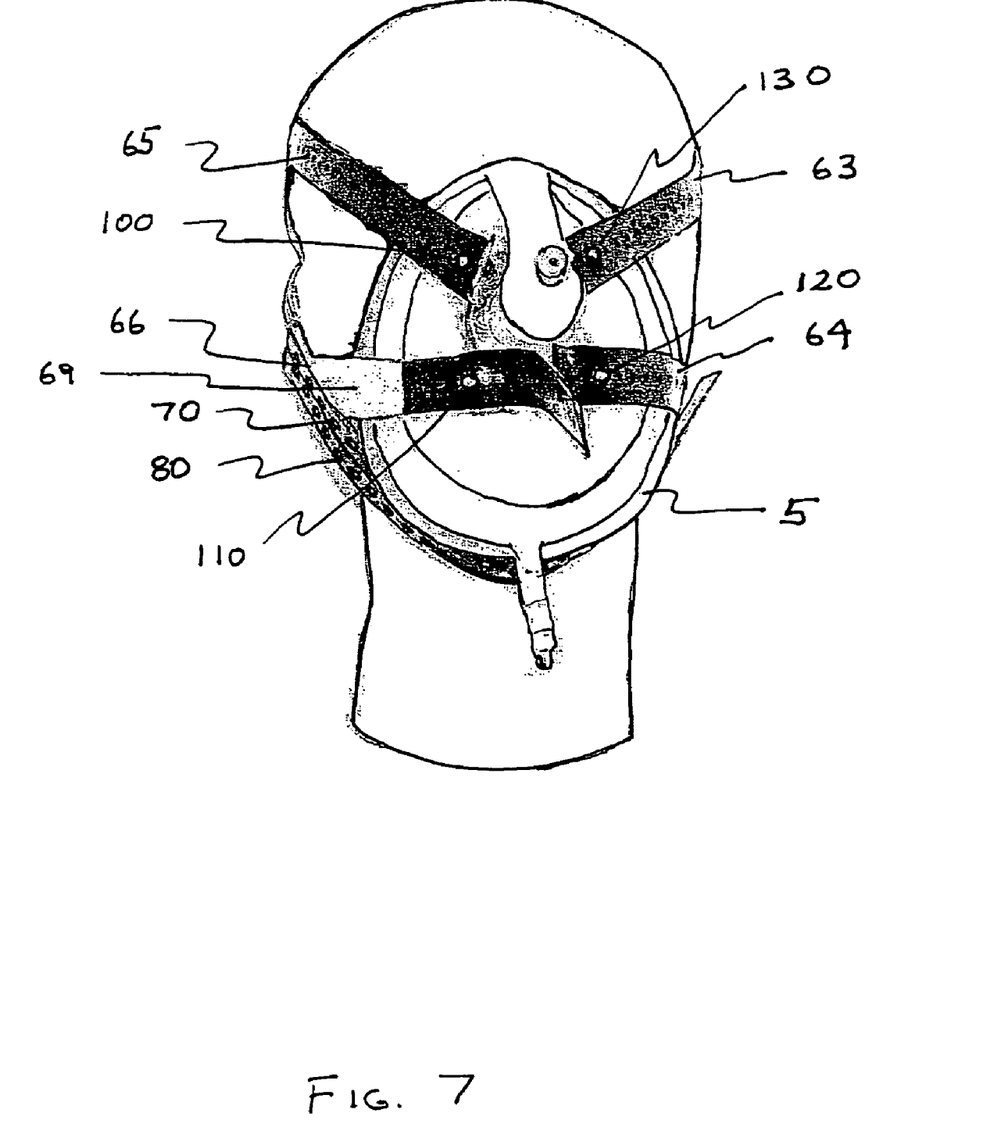
FIG. 7 is a front view of the mask strap, the connecting straps, and the anesthesia mask strapped to a model head according to an embodiment of the present invention.
Figure 8:
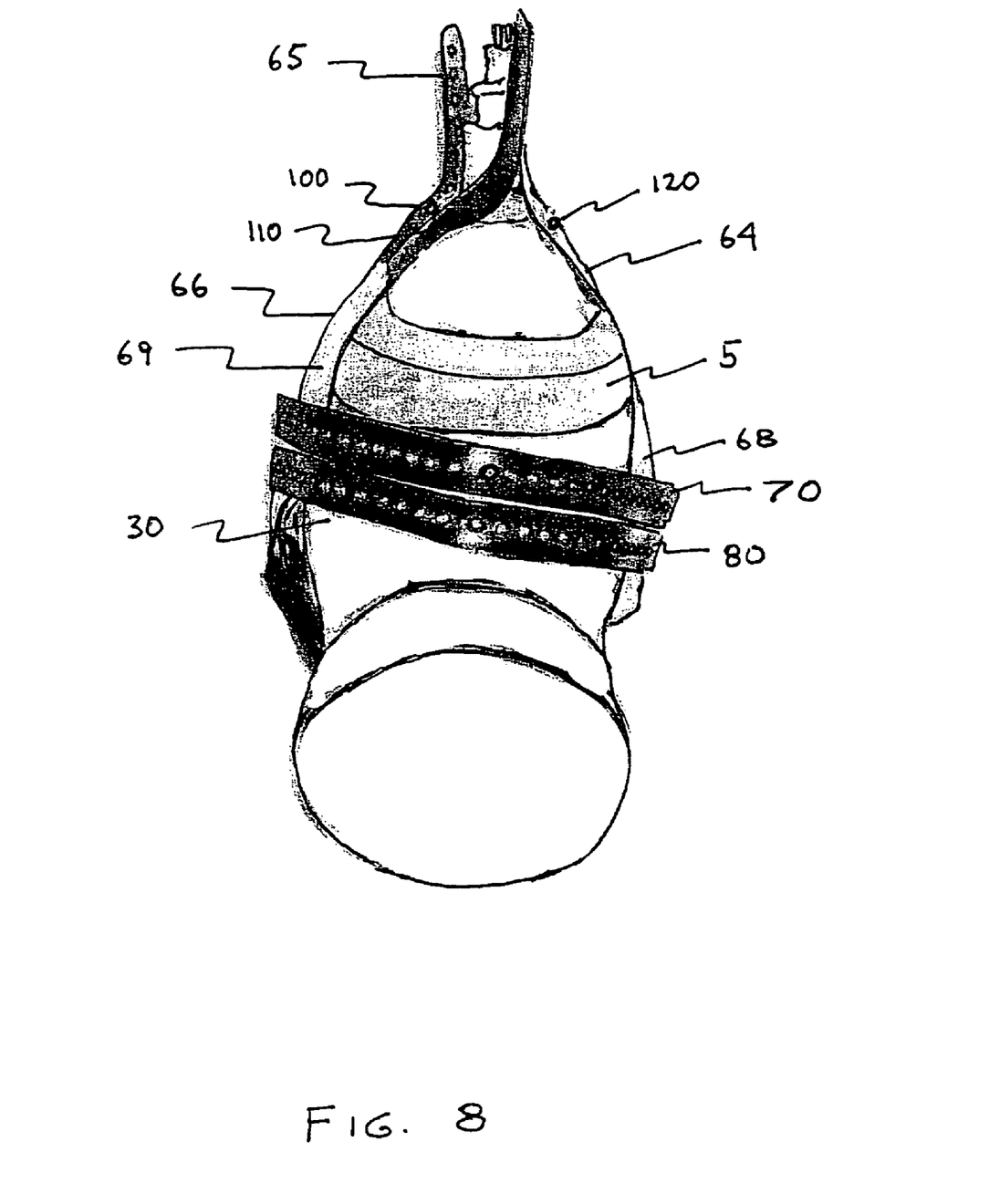
FIG. 8 is a bottom view of the mask strap, the connecting straps, and the anesthesia mask strapped to a model head according to an embodiment of the present invention.

Further, the four narrow extensions 63, 64, 65, and 66 are provided with reinforced holes 67 adapted to engage with protrusions 100, 110, 120, and 130 formed on the mask 5 and shown in FIGS. 6–8. The mask strap 60 can also be attached to the mask 5 using snap fasteners.

Furthermore, the left pair of narrow extensions 64 and 66 are provided with snap fasteners in portions 68 and 69 and the connecting straps 70 and 80 are provided with snap fasteners in portions 73, 76, 83, and 86. In another embodiment of the present invention the right pair of narrow extensions 63 and 65 are also provided with respective portions of snap fasteners and the length of the connecting straps 70 and 80 is extended to reach the right pair of narrow extensions 63 and 65.

Moreover, the left pair of narrow extensions 64 and 66 are used over the patient's temples and the right pair of narrow extensions 63 and 65 are used over the sides of the occipital part of the head of the patient, as shown in FIGS. 6–8, and the connecting straps 70 and 80 connect the left pair of narrow extensions 64 and 66 and travel over the law 30 below the chin point (not shown). The connecting straps 70 and 80 apply the previously described "jaw thrust" maneuver to open the airway without manual assistance of an anesthesia provider.

The portions of snap fasteners 68, 69, 73, 76, 83, and 86 provided on the mask strap 60 and the connecting straps 70 and 80 allow for the adjustment in length on both sides of the connecting straps 70 and 80 so that size adjustments can be made to accommodate different head sizes and shapes. These size adjustments result in the connecting straps applying pressure on the jaw bone without compressing any soft tissue.

In a further embodiment of the present invention the snap fasteners in portions 68, 69, 73, 76, 83, and 86 are replaced with hook-and-loop material so that size adjustments can be made to accommodate different head sizes and shapes.

The mask strap 60 and connecting straps 70 and 80 are preferably made of a non-static latex free rubber material.

Thus, it is apparent that in accordance with the present invention an apparatus that fully satisfies the objectives, aims, and advantages is set forth above. While the invention has been described in conjunction with an specific embodiment, it is evident that many alternatives, modifications, permutations, and variations will become apparent to those skilled in the art in light of the forgoing description. For example, that one connecting strap 70 or 80 could be used instead of two connecting straps 70 and 80.

Accordingly, it is intended that the present invention embrace all such alternatives, modifications and variations as fall within the scope of the appended claims.

I claim:

1. An apparatus for providing anesthesia to a patient, comprising:
    an anesthesia mask including four protrusions;
    a mask strap having a head plate and four narrow extensions each including a plurality of holes adapted to attach to said four protrusions of said anesthesia mask, wherein at least two of said four narrow extensions have respective portions of snap fasteners; and
    a rectangular connecting strap having end portions of snap fasteners attached to said at least two of said four narrow extensions via said respective portions of snap fasteners, wherein said mask strap is adapted to hold said anesthesia mask against a patient's mouth and said rectangular connecting strap is attached only to said mask strap and is adapted to raise the patient's jaw up and forward, thereby unobstructing the patient's airway.

2. The apparatus for providing anesthesia to a patient according to claim 1 further comprising another rectangular connecting strap having end portions of snap fasteners and said other rectangular connecting strap is further attached to said at least two of said four narrow extensions via said respective portions of snap fasteners.

3. The apparatus for providing anesthesia to a patient according to claim 2, wherein said rectangular connecting strap is formed of a non-static latex free rubber material.

4. The apparatus for providing anesthesia to a patient according to claim 1, wherein all of said four narrow extensions have respective portions of snap fasteners.

5. An apparatus for providing anesthesia to a patient, comprising:
    mask means for providing said anesthesia to said patient;
    mask strap means for holding said mask means against a patient's mouth; and
    jaw raising means for raising the patient's jaw up and forward so as to unobstruct the patient's airway, wherein said jaw raising means is attached only to said mask strap means.

6. The apparatus for providing anesthesia to a patient according to claim 5, wherein said jaw raising means is attached to said mask strap means using snap fasteners.

7. The apparatus for providing anesthesia to a patient according to claim 5, wherein said jaw raising means is attached to said mask strap means using hook-and-loop material.

* * * * *